US006180416B1

(12) United States Patent
Kurnik et al.

(10) Patent No.: US 6,180,416 B1
(45) Date of Patent: Jan. 30, 2001

(54) METHOD AND DEVICE FOR PREDICTING PHYSIOLOGICAL VALUES

(75) Inventors: Ronald T. Kurnik, Foster City; Jonathan James Oliver, Oakland; Russell O. Potts; Steven Richard Waterhouse, both of San Francisco; Timothy C. Dunn, Menlo Park; Yalia Jayalakshmi, Sunnyvale; Matthew J. Lesho, San Mateo; Janet A. Tamada, Mountain View; Charles W. Wei, Fremont, all of CA (US)

(73) Assignee: Cygnus, Inc., Redwood City, CA (US)

( * ) Notice: Under 35 U.S.C. 154(b), the term of this patent shall be extended for 0 days.

(21) Appl. No.: 09/163,856

(22) Filed: Sep. 30, 1998

(51) Int. Cl.$^7$ ................................................. G01N 33/553

(52) U.S. Cl. .................. 436/518; 204/400; 204/403; 422/82.01; 422/82.02; 435/14; 435/25; 435/176; 435/287.1; 435/817; 436/525; 436/149; 436/150; 436/151; 436/806

(58) Field of Search .................. 435/14, 25, 176, 435/287.1, 817; 436/518, 525, 149, 150, 151, 806; 422/82.01, 82.02; 204/400, 403

(56) References Cited

U.S. PATENT DOCUMENTS

| 5,279,543 | 1/1994 | Glikfeld et al. . |
| 5,362,307 | 11/1994 | Guy et al. . |
| 5,636,632 | 6/1997 | Bommamman et al. . |
| 5,730,714 | 3/1998 | Guy et al. . |
| 5,735,273 | 4/1998 | Kurnik et al. . |
| 5,771,890 | 6/1998 | Tamada . |
| 5,827,183 | 10/1998 | Kurnik et al. . |
| 5,954,685 | 9/1999 | Tierney . |
| 5,989,409 | 11/1999 | Kurnik et al. . |

FOREIGN PATENT DOCUMENTS

| WO 95/02357 | 1/1995 | (WO) . |
| WO 96/00109 | 1/1996 | (WO) . |
| WO 96/00110 | 1/1996 | (WO) . |
| WO 96/35370 | 11/1996 | (WO) . |
| WO 97/02811 | 1/1997 | (WO) . |
| WO 97/10356 | 3/1997 | (WO) . |
| WO 97/10499 | 3/1997 | (WO) . |
| WO 97/24059 | 7/1997 | (WO) . |
| WO 98/42252 | 10/1998 | (WO) . |
| WO 99/58050 | 11/1999 | (WO) . |
| WO 99/58051 | 11/1999 | (WO) . |
| WO 99/58190 | 11/1999 | (WO) . |
| WO 99/58973 | 11/1999 | (WO) . |

OTHER PUBLICATIONS

Barlow, T.W., "Feed–Forward Neural Networks for Secondary Structure Prediction," *Journal of Molecular Graphics* 13:175–183 (1995).

Ghahramani, Z. And Wolpert, D.M., "Modular Decomposition in Visuomotor Learning," *Nature* 386(6623):392–395 (1997).

Hamilton, J.D. and Susmel, Raul, "Autoregressive Conditional Heteroskedasticity and Changes in Regime," *Journal of Econometrics* 64:307–333 (1994).

(List continued on next page.)

*Primary Examiner*—Christopher L. Chin
(74) *Attorney, Agent, or Firm*—Barbara G. McClung; Robins & Associates

(57) ABSTRACT

The invention relates generally to methods, systems, and devices for measuring the concentration of target analytes present in a biological system using a series of measurements obtained from a monitoring system and a Mixtures of Experts (MOE) algorithm. In one embodiment, the present invention describes a method for measuring blood glucose in a subject.

21 Claims, 2 Drawing Sheets

OTHER PUBLICATIONS

Hu et al., "Customized ECG Beat Classifier Using Mixture of Experts," *Proceedings of the 1995 IEEE Workshop* pp. 459–464 (1995).

Waterhouse, Steven Richard, "Classification and Regression Using Mixtures of Experts," Jesus College, Cambridge and Department of Engineering, University of Cambridge, Oct. 1997.

Weigend et al., "Nonlinear Gated Experts for Time Series: Discovering Regimes and Avoiding Overfitting," *International Journal of Neural Systems* 6(4):373–399 (1995).

Alcok et al., "Continuous Analyte Monitoring to Aid Clinical Practice," *I.E.E.E. Engineering in Medecine & Y Biology*. 13(3):319–325 (1994).

METHOD AND DEVICE FOR PREDICTING PHYSIOLOGICAL VALUES

FIELD OF THE INVENTION

The invention relates generally to a method and device for measuring the concentration of target chemical analytes present in a biological system. More particularly, the invention relates to a method and monitoring systems for predicting a concentration of an analyte using a series of measurements obtained from a monitoring system and a Mixtures of Experts (MOE) algorithm.

BACKGROUND OF THE INVENTION

The Mixtures of Experts model is a statistical method for classification and regression (Waterhouse, S., *"Classification and Regression Using Mixtures of Experts,* October 1997, Ph.D. Thesis, Cambridge University). Waterhouse discusses Mixtures of Experts models from a theoretical perspective and compares them with other models, such as, trees, switching regression models, modular networks. The first extension described in Waterhouse's thesis is a constructive algorithm for learning model architecture and parameters, which is inspired by recursive partitioning. The second extension described in Waterhouse's thesis uses Bayesian methods for learning the parameters of the model. These extensions are compared empirically with the standard Mixtures of Experts model and with other statistical models on small to medium sized data sets. Waterhouse also describes the application of the Mixtures of Experts framework to acoustic modeling within a large vocabulary speech recognition system.

The Mixtures of Experts model has been employed in protein secondary structure prediction (Barlow, T. W., *Journal Of Molecular Graphics,* 13 (3), p. 175–183, 1995). In this method input data were clustered and used to train a series different networks. Application of a Hierarchical Mixtures of Experts to the prediction of protein secondary structure was shown to provide no advantages over a single network.

Mixtures of Experts algorithms have also been applied to the analysis of a variety of different kinds of data sets including the following: human motor systems (Ghahramani, Z. and Wolpert, D. M., *Nature,* 386 (6623): 392–395, 1997); and economic analysis (Hamilton, J. D. and Susmel, R., *Journal of Econometrics,* 64 (1–2): 307–333, 1994).

SUMMARY OF THE INVENTION

The present invention provides a method and device (for example, a monitoring system) for continually or continuously measuring the concentration of an analyte present in a biological system. The method entails continually or continuously detecting a raw signal from the biological system, wherein the raw signal is specifically related to the analyte. As the raw signals are obtained, a calibration step is performed to correlate the raw signal with a measurement value indicative of the concentration of analyte present in the biological system. These steps of detection and calibration are used to obtain a series of measurement values at selected time intervals. Once the series of measurement values is obtained, the method of the invention provides for the prediction of a measurement value using a Mixtures of Experts (MOE) algorithm.

The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the raw signal including, but not limited to, physical, chemical, electrochemical, photochemical, spectrophotometric, polarimetric, calorimetric, radiometric, or like elements. In preferred embodiments of the invention, a biosensor is used which comprises an electrochemical sensing element.

In one particular embodiment of the invention, the raw signal is obtained using a transdermal sampling system that is placed in operative contact with a skin or mucosal surface of the biological system. The sampling system transdermally extracts the analyte from the biological system using any appropriate sampling technique, for example, iontophoresis. The transdermal sampling system is maintained in operative contact with the skin or mucosal surface of the biological system to provide for such continual or continuous analyte measurement.

The analyte can be any specific substance or component that one is desirous of detecting and/or measuring in a chemical, physical, enzymatic, or optical analysis. Such analytes include, but are not limited to, amino acids, enzyme substrates or products indicating a disease state or condition, other markers of disease states or conditions, drugs of abuse, therapeutic and/or pharmacologic agents, electrolytes, physiological analytes of interest (e.g., calcium, potassium, sodium, chloride, bicarbonate ($CO_2$), glucose, urea (blood urea nitrogen), lactate, hematocrit, and hemoglobin), lipids, and the like. In preferred embodiments, the analyte is a physiological analyte of interest, for example glucose, or a chemical that has a physiological action, for example a drug or pharmacological agent.

In a preferred embodiment of the invention, a Mixtures of Experts algorithm is used to predict measurement values. The general Mixtures of Experts algorithm is represented by the following series of equations—where the individual experts have a linear form:

$$An = \sum_{i=1}^{n} An_i w_i \tag{1}$$

wherein (An) is an analyte of interest, n is the number of experts, $An_i$ is the analyte predicted by Expert i; and $w_i$ is a parameter, and the individual experts $An_i$ are further defined by the expression shown as Equation (2)

$$An_i = \sum_{j=1}^{m} a_{ij} P_j + z_i \tag{2}$$

wherein, $An_i$ is the analyte predicted by Expert i; $P_j$ is one of m parameters, m is typically less than 100; $a_{ij}$ are coefficients; and $z_i$ is a constant; and further where the weighting value, $w_i$, is defined by the formula shown as Equation (3).

$$w_i = \frac{e^{d_i}}{\left[\sum_{k=1}^{n} e^{d_k}\right]} \quad (3)$$

where e refers to the exponential function and the $d_k$ (note that the $d_i$ in the numerator of Equation 3 is one of the $d_k$) are a parameter set analogous to Equation 2 that is used to determine the weights $w_i$. The $d_k$ are given by Equation 4.

$$d_k = \sum_{j=1}^{m} \alpha_{jk} P_j + \omega_k \quad (4)$$

where $\alpha_{jk}$ is a coefficient, $P_j$ is one of m parameters, and where $\omega_k$ is a constant.

Another object of the invention to use the Mixtures of Experts algorithm of the invention to predict blood glucose values. In one aspect, the method of the invention is used in conjunction with an iontophoretic sampling device that provides continual or continuous blood glucose measurements. In one embodiment the Mixtures of Experts algorithm is essentially as follows—where the individual experts have a linear form $$BG = w_1 BG_1 + w_2 BG_2 + w_3 BG_3 \quad (5)$$

wherein (BG) is blood glucose, there are three experts (n=3) and $BG_i$ is the analyte predicted by Expert i; $w_i$ is a parameter, and the individual Experts $BG_i$ are further defined by the expression shown as Equations 6, 7, and 8

$$BG_1 = p_1(\text{time}) + q_1(\text{active}) + r_1(\text{signal}) + s_1(BG|cp) + t_1 \quad (6)$$

$$BG_2 = p_2(\text{time}) + q_2(\text{active}) + r_2(\text{signal}) + s_2(BG|cp) + t_2 \quad (7)$$

$$BG_3 = p_3(\text{time}) + q_3(\text{active}) + r_3(\text{signal}) + s_3(BG|cp) + t_3 \quad (8)$$

wherein, $BG_i$ is the analyte predicted by Expert i; parameters include, time (elapsed time), active (active signal), signal (calibrated signal), and BG|cp (blood glucose value at a calibration point); $p_i$, $q_i$, $r_i$, and $s_i$ are coefficients; and $t_i$ is a constant; and further where the weighting value, $w_i$, is defined by the formulas shown as Equations 9, 10, and 11

$$w_1 = \frac{e^{d_1}}{e^{d_1} + e^{d_2} + e^{d_3}} \quad (9)$$

$$w_2 = \frac{e^{d_2}}{e^{d_1} + e^{d_2} + e^{d_3}} \quad (10)$$

$$w_3 = \frac{e^{d_3}}{e^{d_1} + e^{d_2} + e^{d_3}} \quad (11)$$

where e refers to the exponential function and $d_i$ is a parameter set (analogous to Equations 6, 7, and 8) that are used to determine the weights $w_i$, given by Equations 9, 10, and 11, and $$d_1 = \tau_1(\text{time}) + \beta_1(\text{active}) + \gamma_1(\text{signal}) + \delta_1(BG|cp) + \epsilon_1 \quad (12)$$

$$d_2 = \tau_2(\text{time}) + \beta_2(\text{active}) + \gamma_2(\text{signal}) + \delta_2(BG|cp) + \epsilon_2 \quad (13)$$

$$d_3 = \tau_3(\text{time}) + \beta_3(\text{active}) + \gamma_3(\text{signal}) + \delta_3(BG|cp) + \epsilon_3 \quad (14)$$

where $\tau_i$, $\beta_i$, $\gamma_i$ and $\delta_i$ are coefficients, and where $\epsilon_i$ is a constant.

Other parameters that can be included in these calculations include, but are not limited to, temperature, iontophoretic voltage, and skin conductivity.

A further object of the invention to provide a method for measuring blood glucose in a subject. The method entails operatively contacting a glucose sensing apparatus with the subject to detect blood glucose and thus obtain a raw signal from the sensing apparatus. The raw signal is specifically related to the glucose, and is converted into a measurement value indicative of the subject's blood glucose concentration using a calibration step. In one aspect of the invention, the sensing apparatus is a near-IR spectrometer.

It is also an object of the invention to provide a monitoring system for continually or continuously measuring an analyte present in a biological system. The monitoring system is formed from the operative combination of a sampling means, a sensing means, and a microprocessor means which controls the sampling means and the sensing means. The sampling means is used to continually or continuously extract the analyte from the biological system across a skin or mucosal surface of said biological system. The sensing means is arranged in operative contact with the analyte extracted by the sampling means, such that the sensing means can obtain a raw signal from the extracted analyte which signal is specifically related to the analyte. The microprocessor means communicates with the sampling means and the sensing means, and is used to: (a) control the sampling means and the sensing means to obtain a series of raw signals at selected time intervals during a continual or continuous measurement period; (b) correlate the raw signals with measurement values indicative of the concentration of analyte present in the biological system; and (c) predict a measurement value using the Mixtures of Experts algorithm. In one aspect, the monitoring system uses an iontophoretic current to extract the analyte from the biological system.

It is a further object of the invention to provide a monitoring system for measuring blood glucose in a subject. The monitoring system is formed from an operative combination of a sensing means and a microprocessor means. The sensing means is adapted for operative contact with the subject or with a glucose-containing sample extracted from the subject, and is used to obtain a raw signal specifically related to blood glucose in the subject. The microprocessor means communicates with the sensing means, and is used to: (a) control the sensing means to obtain a series of raw signals (specifically related to blood glucose) at selected time intervals; (b) correlate the raw signals with measurement values indicative of the concentration of blood glucose present in the subject; and (c) predict a measurement value using the Mixtures of Experts algorithm.

In a further aspect, the monitoring system comprises a biosensor having an electrochemical sensing element. In another aspect, the monitoring system comprises a near-IR spectrometer.

Additional objects, advantages and novel features of the invention will be set forth in part in the description which follows, and in part will become apparent to those skilled in the art upon examination of the following, or may be learned by practice of the invention.

DETAILED DESCRIPTION OF THE PREFERRED EMBODIMENTS

Figure 1A:
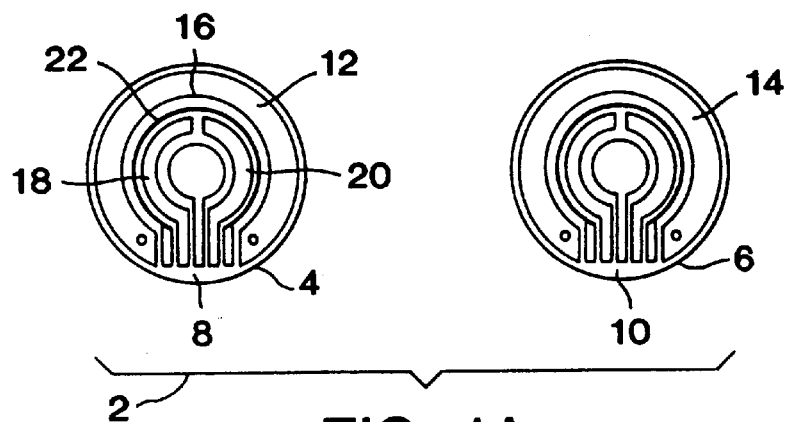
FIG. 1A depicts a top plan view of an iontophoretic collection reservoir and electrode assembly for use in a transdermal sampling device constructed according to the present invention.

Before describing the present invention in detail, it is to be understood that this invention is not limited to particular compositions or biological systems, as such may vary. It is also to be understood that the terminology used herein is for the purpose of describing particular embodiments only, and is not intended to be limiting.

It must be noted that, as used in this specification and the appended claims, the singular forms "all", "an" and "the" include plural referents unless the content clearly dictates otherwise. Thus, for example, reference to "an analyte" includes mixtures of analytes, and the like.

All publications, patents and patent applications cited herein, whether supra or infra, are hereby incorporated by reference in their entirety.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

Definitions

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte. Furthermore, the terms "analyte" and "substance" are used interchangeably herein, and are intended to have the same meaning, and thus encompass any substance of interest. In preferred embodiments, the physiological analyte of interest is, for example, glucose, or a chemical that has a physiological action, for example a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, typically of animal nature, such as natural or artificial skin, blood vessel tissue, intestinal tissue, and the like. A "biological system" thus includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 27, 1997); and WO 97/43962 (published Nov. 27, 1997). Laser devices use a small laser beam to punch a hole through the upper layer of the patient's skin (see, e.g., Jacques et al. (1978) *J. Invest. Dermatology* 88:88–93). Examples of invasive sampling techniques include traditional needle and syringe or vacuum sample tube devices.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example by establishing an electrical potential using a direct current (DC) between fixed anode and cathode iontophoretic electrodes, alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike et al. (1967) *Nature* 214:986–988) and other amperometric, coulometric, or potentiometric electrochemical devices. Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips et al.).

A "sensing electrode" refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum, palladium, rhodium, ruthenium, nickel, carbon, noble metals (e.g., gold), and oxides, dioxides and combinations or alloys thereof.

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

The term "collection reservoir" is used to describe any suitable containment means for containing a sample extracted from a biological system. The reservoir can include a material which is tonically conductive (e.g., water with ions therein), wherein another material such as a sponge-like material or hydrophilic polymer is used to keep the water in place. Such collection reservoirs can be in the form of a hydrogel (for example, in the shape of a disk or pad). Other suitable collection reservoirs include, but are not limited to, tubes, vials, capillary collection devices, cannulas, and miniaturized etched, ablated or molded flow paths.

An "ionically conductive material" refers to any material that provides ionic conductivity, and through which electrochemically active species can diffuse. The tonically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

A "Mixtures of Experts (MOE)" algorithm is used in the practice of the present invention. An example of a Mixtures of Experts algorithm useful in connection with the present invention is represented by the following equations, where the individual experts have a linear form:

$$An = \sum_{i=1}^{n} An_i w_i \qquad (1)$$

wherein (An) is an analyte of interest, n is the number of experts, $An_i$ is the analyte predicted by Expert i; and $w_i$ is a parameter, and the individual experts $An_i$ are further defined by the expression shown as Equation (2)

$$An_i = \sum_{j=1}^{m} a_{ij} P_j + z_i \qquad (2)$$

wherein, $An_i$ is the analyte predicted by Expert i; $P_j$ is one of m parameters, m is typically less than 100; $a_{ij}$ are coefficients; and $z_i$ is a constant; and further where the weighting value, $w_i$, is defined by the formula shown as Equation (3).

$$w_i = \frac{e^{d_i}}{\left[\sum_{k=1}^{n} e^{d_k}\right]} \qquad (3)$$

where e refers to the exponential function the $d_k$ (note that the $d_i$ in the numerator of Equation 3 is one of the d) are a parameter set analogous to Equation 2 that is used to determine the weights $w_i$. The $d_k$ are given by Equation 4.

$$d_k = \sum_{j=1}^{m} \alpha_{jk} P_j + \omega_k \qquad (4)$$

where $\alpha_{jk}$ is a coefficient, $P_j$ is one of m parameters, and where $\omega_k$ is a constant.

The Mixtures of Experts algorithm is a generalized predictive technology for data analysis. This method uses a superposition of multiple linear regressions, along with a switching algorithm, to predict outcomes. Any number of input/output variables are possible. The unknown coefficients in this method are determined by a maximum posterior probability technique.

The method is typically implemented as follows. An experimental data set of input/output pairs is assembled that spans the expected ranges of all variables. These variables are then used to train the Mixtures of Experts (that is, used to determine the unknown coefficients). These coefficients are determined using, for example, the Expectation Maximization method (Dempster, A. P., N. M. Laird, and D. B. Rubin, *J. Royal Statistical Society* (Series B-Methodological) 39: (1), 1977). Once these coefficients are known, the Mixtures of Experts is easily applied to a new data set.

"Parameter" as used herein refers to an arbitrary constant or variable so appearing in a mathematical expression that changing it give various cases of the phenomenon represented (*McGraw-Hill Dictionary of Scientific and Technical Terms,* S. P. Parker, ed., Fifth Edition, McGraw-Hill Inc., 1994). In the context of the GlucoWatch® monitor (Cygnus, Inc., Redwood City, Calif.), a parameter is a variable that influences the value of the blood glucose level as calculated by an algorithm. For the Mixtures of Experts algorithm, these parameters include, but are not limited to, the following: elapsed time since the monitor was applied to a subject; the active signal; the calibrated signal; the blood glucose value at the calibration point; the skin temperature; the skin conductivity; and the iontophoretic voltage. Changes in the values of any of these parameters can be expected to change the value of the calculated blood glucose value.

General Methods

The present invention relates to use of a sensing device for measuring the concentration of a target analyte present in a biological system. In preferred embodiments, the sensing device comprises a biosensor. In other preferred embodiments, a sampling device is used to extract small amounts of a target analyte from the biological system, and then sense and/or quantify the concentration of the target analyte. Measurement with the biosensor and/or sampling with the sampling device can be carried out in a continual manner. Continual measurement allows for closer monitoring of target analyte concentration fluctuations.

In the general method of the invention, a raw signal is obtained from a sensing device, which signal is related to a target analyte present in the biological system. The raw signal can be obtained using any suitable sensing methodology including, for example, methods which rely on direct contact of a sensing apparatus with the biological system; methods which extract samples from the biological system by invasive, minimally invasive, and non-invasive sampling techniques, wherein the sensing apparatus is contacted with the extracted sample; methods which rely on indirect contact of a sensing apparatus with the biological system; and the like. In preferred embodiments of the invention, methods are used to extract samples from the biological sample using minimally invasive or non-invasive sampling techniques. The sensing apparatus used with any of the above-noted methods can employ any suitable sensing element to provide the signal including, but not limited to, physical, chemical, electrochemical, photochemical, spectrophotometric, polarimetric, calorimetric, radiometric, or like elements. In preferred embodiments of the invention, a biosensor is used which comprises an electrochemical sensing element.

In another embodiment of the invention, a near-IR glucose sensing apparatus is used to detect blood glucose in a subject, and thus generate the raw signal. A number of near-IR glucose sensing devices suitable for use in the present method are known in the art and are readily available. For example, a near-IR radiation diffuse-reflection laser spectroscopy device is described in U.S. Pat. No. 5,267,152 to Yang et al. Similar near-IR spectrometric devices are also described in U.S. Pat. No. 5,086,229 to Rosenthal et al. and U.S. Pat. No. 4,975,581 to Robinson et al. These near-IR devices use traditional methods of reflective or transmissive near infrared (near-IR) analysis to measure absorbance at one or more glucose-specific wavelengths, and can be contacted with the subject at an appropriate location, such as a finger-tip, skin fold, eyelid, or forearm surface to obtain the raw signal.

The raw signal obtained using any of the above-described methodologies is then converted into an analyte-specific value of known units to provide an interpretation of the signal obtained from the sensing device. The interpretation uses a mathematical transformation to model the relationship between a measured response in the sensing device and a corresponding analyte-specific value (in the present invention, a Mixtures of Experts algorithm). Thus, a calibration step is used herein to relate, for example, an electrochemical signal (detected by a biosensor), or near-IR absorbance spectra (detected with a near-IR detector) with the concentration of a target analyte in a biological system.

The predicted analyte values can optionally be used in a subsequent step to control an aspect of the biological system. In one embodiment, predicted analyte values are used to determine when, and at what level, a constituent should be added to the biological system in order to control an aspect of the biological system. In a preferred embodiment, the analyte value can be used in a feedback control loop to control a physiological effect in the biological system.

The above general methods can, of course, be used with a wide variety of biological systems, target analytes, and/or sensing techniques. The determination of particularly suitable combinations is within the skill of the ordinarily skilled artisan when directed by the instant disclosure. Although these methods are broadly applicable to measuring any chemical analyte and/or substance in a biological system, the invention is expressly exemplified for use in a non-invasive, transdermal sampling system which uses an electrochemical biosensor to quantify or qualify glucose or a glucose metabolite.

Obtaining the Raw Signal.

The raw signal can be obtained using any sensing device that is operatively contacted with the biological system. Such sensing devices can employ physical, chemical, electrochemical, spectrophotometric, polarimetric, calorimetric, radiometric, or like measurement techniques. In addition, the sensing device can be in direct or indirect contact with the biological system, or used with a sampling device which extracts samples from the biological system using invasive, minimally invasive or non-invasive sampling techniques. In preferred embodiments, a minimally invasive or non-invasive sampling device is used to obtain samples from the biological system, and the sensing device comprises a biosensor with an electrochemical sensing element. In particularly preferred embodiments, a sampling device is used to obtain continual transdermal or transmucosal samples from a biological system, and the analyte of interest is glucose.

More specifically, a non-invasive glucose monitoring device is used to measure changes in glucose levels in an animal subject over a wide range of glucose concentrations. The sampling method is based on transdermal glucose extraction and the sensing method is based on electrochemical detection technology. The device can be contacted with the biological system continuously, and automatically obtains glucose samples in order to measure glucose concentration at preprogrammed intervals.

Sampling is carried out continually by non-invasively extracting glucose through the skin of the patient using an iontophoretic current. More particularly, an iontophoretic current is applied to a surface of the skin of a subject. When the current is applied, ions or charged molecules pull along other uncharged molecules or particles such as glucose which are drawn into a collection reservoir placed on the surface of the skin. The collection reservoir may comprise any ionically conductive material and is preferably in the form of a hydrogel which is comprised of a hydrophilic material, water and an electrolyte. The collection reservoir may further contain an enzyme which catalyzes a reaction between glucose and oxygen. The enzyme is preferably glucose oxidase (GOx) which catalyzes the reaction between glucose and oxygen and results in the production of hydrogen peroxide. The hydrogen peroxide reacts at a catalytic surface of a biosensor electrode, resulting in the generation of electrons which create a detectable biosensor current (raw signal). Based on the amount of biosensor current created over a given period of time, a measurement is taken, which measurement is related to the amount of glucose drawn into the collection reservoir over a given period of time. In a preferred embodiment the reaction is allowed to continue until substantially all of the glucose in the collection reservoir has been subjected to a reaction and is therefore no longer detectable, and the total biosensor current generated is related to the concentration of glucose in the subject.

When the reaction is complete, the process is repeated and a subsequent measurement is obtained. More specifically, the iontophoretic current is again applied, glucose is drawn through the skin surface into the collection reservoir, and the reaction is catalyzed in order to create a biosensor current. These sampling (extraction) and sensing operations are integrated such that glucose from interstitial fluid directly beneath the skin surface is extracted into the hydrogel collection pad where it contacts the GOx enzyme. The GOx enzyme converts glucose and oxygen in the hydrogel to hydrogen peroxide which diffuses to a Pt-based sensor and reacts with the sensor to regenerate oxygen and form electrons. The electrons generate an electrical signal that can be measured, analyzed, and correlated to blood glucose.

A generalized method for continual monitoring of a physiological analyte is disclosed in International Publication No. WO 97/24059, published Jul. 10, 1997, which publication is incorporated herein by reference. As noted in that publication, the analyte is extracted into a reservoir containing a hydrogel which is preferably comprised of a hydrophilic material of the type described in International Publication No. WO 97/02811, published Jan. 30, 1997, which publication is incorporated herein by reference. Suitable hydrogel materials include polyethylene oxide polyacrylic acid, polyvinylalcohol and related hydrophilic polymeric materials combined with water to form an aqueous gel.

In the above non-invasive glucose monitoring device, a biosensor electrode is positioned on a surface of the hydrogel opposite the surface contacting the skin. The sensor electrode acts as a detector which detects current generated by hydrogen peroxide in the redox reaction, or more specifically detects current which is generated by the electrons generated by the redox reaction catalyzed by the platinum surface of the electrode. The details of such electrode assemblies and devices for iontophoretic extraction of glucose are disclosed in International Publication No. WO 96/00110, published Jan. 4, 1996, and International Publication No. WO 97/10499, published Mar. 2, 1997, which publications are also incorporated herein by reference.

Figure 1B:
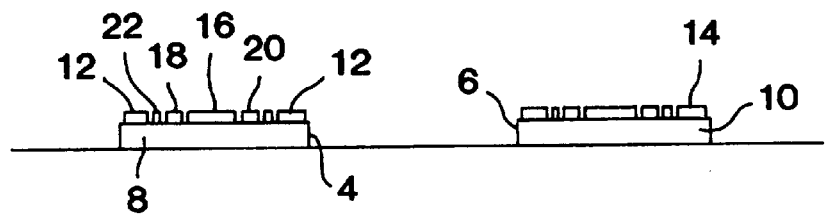
FIG. 1B depicts the side view of the iontophoretic collection reservoir and electrode assembly shown in FIG. 1A.

Referring now to FIGS. 1A and 1B, one example of an iontophoretic collection reservoir and electrode assembly for use in a transdermal sensing device is generally indicated at 2. The assembly comprises two iontophoretic collection reservoirs, 4 and 6, each having a conductive medium 8, and 10 (preferably cylindrical hydrogel pads), respectively disposed therein. First (12) and second (14) ring-shaped iontophoretic electrodes are respectively contacted with conductive medium 8 and 10. The first iontophoretic electrode 12 surrounds three biosensor electrodes which are also contacted with the conductive medium 8, a working electrode 16, a reference electrode 18, and a counter electrode 20. A guard ring 22 separates the biosensor electrodes from the iontophoretic electrode 12 to minimize noise from the iontophoretic circuit. Conductive contacts provide communication between the electrodes and an associated power source and control means as described in detail below. A similar biosensor electrode arrangement can be contacted with the conductive medium 10, or the medium can not have a sensor means contacted therewith.

Figure 2:
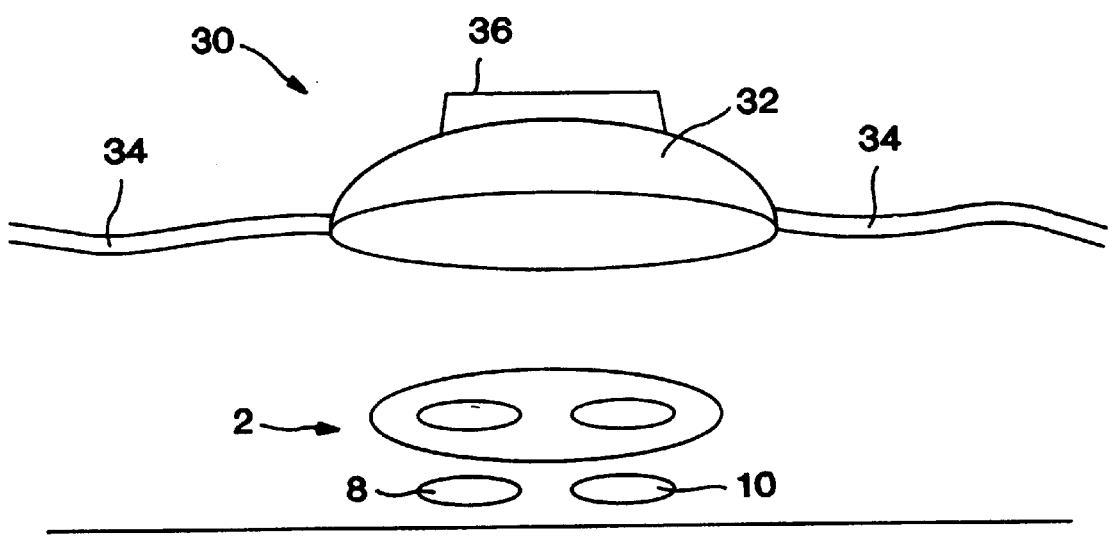
FIG. 2 is a pictorial representation of an iontophoretic sampling device which includes the iontophoretic collection reservoir and electrode assembly of FIGS. 1A and 1B.

Referring now to FIG. 2, the iontophoretic collection reservoir and electrode assembly 2 of FIGS. 1A and 1B is shown in exploded view in combination with a suitable iontophoretic sampling device housing 32. The housing can be a plastic case or other suitable structure which preferably is configured to be worn on a subjects arm in a manner similar to a wrist watch. As can be seen, conductive media 8 and 10 (hydrogel pads) are separable from the assembly 2; however, when the assembly 2 and the housing 32 are assembled to provide an operational iontophoretic sampling device 30, the media are in contact with the electrodes to provide a electrical contact therewith.

A power source (e.g., one or more rechargeable or non-rechargeable batteries) can be disposed within the housing 32 or within the straps 34 which hold the device in contact with a skin or mucosal surface of a subject. In use, an electric potential (either direct current or a more complex waveform) is applied between the two iontophoretic electrodes 12 and 14 such that current flows from the first iontophoretic electrode 12, through the first conductive medium 8 into the skin or mucosal surface, and then back out through the second conductive medium 10 to the second iontophoretic electrode 14. The current flow is sufficient to extract substances including an analyte of interest through the skin into one or both of collection reservoirs 4 and 6. The electric potential may be applied using any suitable technique, for example, the applied current density may be in the range of about 0.01 to 0.5 $mA/cm^2$. In a preferred embodiment, the device is used for continual or continuous monitoring, and the polarity of iontophoretic electrodes 12 and 14 is alternated at a rate of about one switch every 10 seconds to about one switch every hour so that each electrode is alternately a cathode or an anode. The housing 32 can further include an optional temperature sensing element (e.g., a thermistor, thermometer, or thermocouple device) which monitors the temperature at the collection reservoirs to enable temperature correction of sensor signals. The housing can also include an optional conductance sensing element (e.g., an integrated pair of electrodes) which monitors conductance at the skin or mucosal surface to enable data screening correction or invalidation of sensor signals.

After a suitable iontophoretic extraction period, one or both of the sensor electrode sets can be activated in order to detect extracted substances including the analyte of interest. Operation of the iontophoretic sampling device 30 can be controlled by a controller 36 (e.g., a microprocessor), which interfaces with the iontophoretic electrodes, the sensor electrodes, the power supply, the optional temperature and/ or conductance sensing elements, a display and other electronics. For example, the controller 36 can include a programmable a controlled circuit source/sink drive for driving the iontophoretic electrodes. Power and reference voltage are provided to the sensor electrodes, and signal amplifiers can be used to process the signal from the working electrode or electrodes. In general, the controller discontinues the iontophoretic current drive during sensing periods. A sensor confidence loop can be provided for continually monitoring the sampling system to insure proper operations.

User control can be carried out using push buttons located on the housing 32, and an optional liquid crystal display (LCD) can provide visual prompts, readouts and visual alarm indications. The microprocessor generally uses a series of program sequences to control the operations of the sampling device, which program sequences can be stored in the microprocessor's read only memory (ROM). Embedded software (firmware) controls activation of measurement and display operations, calibration of analyte readings, setting and display of high and low analyte value alarms, display and setting of time and date functions, alarm time, and display of stored readings. Sensor signals obtained from the sensor electrodes can be processed before storage and display by one or more signal processing functions or algorithms which are stored in the embedded software. The microprocessor can also include an electronically erasable, programmable, read only memory (EEPROM) for storing calibration parameters, user settings and all downloadable sequences. A serial communications port allows the device to communicate with associated electronics, for example, wherein the device is used in a feedback control application to control a pump for delivery of a medicament.

Converting to an Analyte-Specific Value.

The raw signal is then converted into an analyte-specific value using a calibration step which correlates the signal obtained from the sensing device with the concentration of the analyte present in the biological system. A wide variety of calibration techniques can be used to interpret such signals. These calibration techniques apply mathematical, statistical and/or pattern recognition techniques to the problem of signal processing in chemical analyses, for example, using neural networks, genetic algorithm signal processing, linear regression, multiple-linear regression, or principal components analysis of statistical (test) measurements.

One method of calibration involves estimation techniques. To calibrate an instrument using estimation techniques, it is necessary to have a set of exemplary measurements with known concentrations referred to as the calibration set (e.g., reference set). This set consists of S samples, each with m instrument variables contained in an S by m matrix (X), and an S by 1 vector (y), containing the concentrations. If a priori information indicates the relationship between the measurement and concentration is linear, the calibration will attempt to determine an S by 1 transformation or mapping (b), such that y=Xb, is an optimal estimate of y according to a predefined criteria. Numerous suitable estimation techniques useful in the practice of the invention are known in the art. These techniques can be used to provide correlation factors (e.g., constants), which correlation factors are then used in a mathematical transformation to obtain a measurement value indicative of the concentration of analyte present in the biological system at the times of measurement.

In one particular embodiment, the calibration step can be carried out using artificial neural networks or genetic algorithms. The structure of a particular neural network algorithm used in the practice of the invention can vary widely; however, the network should contain an input layer, one or more hidden layers, and one output layer. Such networks can be trained on a test data set, and then applied to a population. There are an infinite number of suitable network types, transfer functions, training criteria, testing and application methods which will occur to the ordinarily skilled artisan upon reading the instant specification. In the context of the iontophoretic glucose sampling device described hereinabove (which contains an active collection reservoir—with the GOx enzyme, and a blank collection reservoir), a neural network algorithm could use the following inputs to provide a blood glucose measurement: time; signal from the active reservoir; signal from the blank reservoir; calibration time; skin temperature; voltage; skin conductivity; and, when operating in the training mode, measured glucose (use of exemplary inputs are presented in Examples 1 and 2).

Predicting Measurements

The analyte-specific values obtained using the above techniques are used herein to predict target analyte concentrations in a biological system using a Mixtures of Experts (MOE) analysis.

The Mixtures of Experts algorithm breaks up a non-linear prediction equation into several linear prediction equations ("Experts"). An "Expert" routine is then used to switch between the different linear equations. In the equations presented below, the w (weighting) factor determines the switch by weighting the different Experts with a number between 0 and 1, with the restriction that:

$$\sum_{i=1}^{n} w_i = 1$$

The Mixtures of Experts algorithm of the present invention is based on the ideal case presented in Equation 1, where the individual experts have a linear form:

$$An = \sum_{i=1}^{n} An_i w_i \qquad (1)$$

wherein (An) is an analyte of interest, n is the number of experts, $An_i$ is the analyte predicted by Expert i; and $w_i$ is a parameter. The number of experts is chosen based on the quality of the fit of the model, subject to the requirement that it is desirable to use the least number of experts possible. The number of experts is preferably less than 100, and more preferably less than 30. In most cases, selection of the fewest possible experts is desirable.

The individual Experts $An_i$ are further defined by the expression shown as Equation (2).

$$An_i = \sum_{j=1}^{m} a_{ij} P_j + z_i \qquad (2)$$

wherein, $An_i$ is the analyte predicted by Expert i; $P_j$ is one of m parameters, m is typically less than 100; $a_{ij}$ are coefficients; and $z_i$ is a constant.

The weighting value, $w_i$, is defined by the formula shown as Equation (3).

$$w_i = \frac{e^{d_i}}{\left[\sum_{k=1}^{n} e^{d_k}\right]} \quad (3)$$

where e refers to the exponential function and the $d_k$ (note that the $d_i$ in the numerator of Equation 3 is one of the $d_k$) are a parameter set analogous to Equation 2 that is used to determine the weights $w_i$. The $d_k$ are given by Equation 4.

$$d_k = \sum_{j=1}^{m} \alpha_{jk} P_j + \omega_k \quad (4)$$

where $\alpha_{jk}$ is a coefficient, $P_j$ is one of m parameters, and where $\omega_k$ is a constant.

The Mixtures of Experts method described by the above equations is supplied with a large data base of empirically obtained information about the parameters defined by the equations. By employing a linear regression function, the equations are simultaneously solved for the values of all coefficients and constants. In other words, the algorithm is trained to be predictive for the value of An (the analyte) given a particular set of data. A preferred optimization method to determine the coefficients and constants is the Expectation Maximization method (Dempster, A. P., N. M. Laird, and D. B. Rubin, *J. Royal Statistical Society* (Series B-Methodological) 39: (1), 1977). Other optimization methods include the Levenburg-Marquardt algorithm (Marquardt, D. W., *J. Soc. Ind. Appl. Math.* 11:p431–441, 1963) and the Simplex algorithm (Nelder, J. A., and Mead, R., *Computer Journal* 7:p308, 1965).

In the context of blood glucose monitoring with an iontophoretic sampling device, the MOE algorithm allows for the accurate prediction of glucose concentration. In this regard, during a typical iontophoretic measuring cycle, iontophoretic extraction of the analyte is carried out for a suitable amount of time, for example about 1 to 30 minutes, after which time the extracted analyte is detected for a suitable amount of time, for example about 1–30 minutes. An application of the Mixtures of Experts algorithm to a specific set of parameters for glucose monitoring is presented in Example 1.

In the context of blood glucose monitoring with an iontophoretic sampling device, the Mixtures of Experts algorithm allows for the accurate prediction of blood glucose concentrations.

EXAMPLES

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Application of the "Mixtures of Experts" to Glucose Monitoring

This example describes the use of a Mixtures of Experts (MOE) algorithm to predict blood glucose data from a series of signals.

In the present example, a GlucoWatch® monitor was used to collect data and the following variables were chosen to generate data sets for the MOE algorithm:

1) elapsed time (time)—elapsed time since the watch was applied to the subject;

2) active signal (active), in this example, the value of the active parameter corresponded to the nanoamp signal that was integrated over the sensing time-interval to give the active parameter in nanocoulombs (nC);

3) calibrated signal (signal), in this example was obtained by multiplying an active by a constant, where the constant was defined as the blood glucose level at the calibration point divided by the active value at the calibration point. For example, as follows:

$$\text{signal} = \frac{BG|cp}{\text{active}|cp}(\text{active})$$

where the slope of the line active versus blood glucose had a non-zero intercept and the offset took into account that the intercept was not zero. In the alternative, the constant could be as follows:

$$\text{signal} = \frac{BG|cp}{(\text{active}|cp + \text{offset})}(\text{active} + \text{offset})$$

where the offset takes into account the intercept value.

4) blood glucose value at the calibration point (BG|cp) was determined by direct blood testing.

Other possible variables include, but are not limited to, temperature, iontophoretic voltage (which is inversely proportional to skin resistance), and skin conductivity.

Large data sets were generated by collecting signals using a transdermal sampling system that was placed in operative contact with the skin. The sampling system transdermally extracted the analyte from the biological system using an appropriate sampling technique—iontophoresis. The transdermal sampling system was maintained in operative contact with the skin to provide a near continual or continuous stream of signals.

The basis of the Mixtures of Experts was to break up a non-linear prediction equation (Equation 5, below) into several Expert prediction equations, and then to have a routine to switch between the different linear equations. For predicting blood glucose levels, three separate linear equations (Equations 6, 7, and 8) were used to represent blood glucose, with the independent variables discussed above of time, active, signal, blood glucose at a calibration point (BG|cp), and a constant ($t_i$).

The switching between equations 6, 7, and 8 was determined by the parameters $w_1$, $w_2$, and $w_3$ in equation 5, which was further determined by the parameters $d_1$, $d_2$, and $d_3$ as given by equations 9–14, where the individual experts had a linear form:

$$BG = w_1 BG_1 + w_2 BG_2 + w_3 BG_3 \quad (5)$$

wherein (BG) was blood glucose, there are three experts (n=3); $BG_i$ was the analyte predicted by Expert i; and $w_i$ was a parameter, and the individual Experts $BG_i$ were further defined by the expression shown as Equations 6, 7, and 8

$$BG_1 = p_1(\text{time}) + q_1(\text{active}) + r_1(\text{signal}) + s_1(BG|cp) + t_1 \quad (6)$$

$$BG_2 = p_2(\text{time}) + q_2(\text{active}) + r_2(\text{signal}) + s_2(BG|cp) + t_2 \quad (7)$$

$$BG_3 = p_3(\text{time}) + q_3(\text{active}) + r_3(\text{signal}) + s_3(BG|cp) + t_3 \quad (8)$$

wherein, $BG_i$ was the analyte predicted by Expert i; parameters include, time (elapsed time), active (active signal), signal (calibrated signal), and $BG|cp$ (blood glucose value at a calibration point); $p_i$, $q_i$, $r_i$, and $s_i$ were coefficients; and $t_i$ was a constant; and further where the weighting value, $w_i$, was defined by the formulas shown as Equations 9, 10, and 11

$$w_1 = \frac{e^{d_1}}{e^{d_1} + e^{d_2} + e^{d_3}} \quad (9)$$

$$w_2 = \frac{e^{d_2}}{e^{d_1} + e^{d_2} + e^{d_3}} \quad (10)$$

$$w_3 = \frac{e^{d_3}}{e^{d_1} + e^{d_2} + e^{d_3}} \quad (11)$$

where e refered to the exponential function and $d_i$ was a parameter set (analogous to Equations 6, 7, and 8) that were used to determine the weights $w_i$, given by Equations 9, 10, and 11, and $$d_1 = \tau_1(\text{time}) + \beta_1(\text{active}) + \gamma_1(\text{signal}) + \delta_1(BG|cp) + \epsilon_1 \quad (12)$$

$$d_2 = \tau_2(\text{time}) + \beta_2(\text{active}) + \gamma_2(\text{signal}) + \delta_2(BG|cp) + \epsilon_2 \quad (13)$$

$$d_3 = \tau_3(\text{time}) + \beta_3(\text{active}) + \gamma_3(\text{signal}) + \delta_3(BG|cp) + \epsilon_3 \quad (14)$$

where $\tau_i$, $\beta_i$, $\gamma_i$ and $\delta_i$ were coefficients, and where $\epsilon_1$ is a constant.

To calculate the above parameters an optimization method was applied to the algorithm (Equations 5–14) and the large data set. The optimization method used was the Expectation Maximization method (Dempster, A. P., N. M. Laird, and D. B. Rubin, *J. Royal Statistical Society* (Series B-Methodological) 39: (1), 1977), but other methods may be used as well.

The parameters in these equations were determined such that the posterior probability of the actual glucose was maximized.

Example 2

Prediction of Measurement Values

Iontophoretic extraction of glucose was carried out using a GlucoWatch® monitor which employs (i) a low-level iontophoretic current to extract glucose through patient's skin, and (ii) an electrochemical biosensor to detect the extracted glucose. Iontophoresis was carried out for 3 minute intervals and electrochemical detection was carried out for 7 minute intervals to result in 10 minute measurement cycles—thus generating collections of data (data sets) as described in Example 1.

The data that were used for this analysis were obtained by diabetic subjects each wearing a GlucoWatch® monitor over a 14 hour period. The MOE inputs consisted of the following parameters (described in Example 1): time, active, signal, blood glucose at a calibration point (BG|cp). These training data were used to determine the unknown parameters in the MOE using the Expectation Maximization Method. The output of the MOE algorithm was the measured value of blood glucose. Using a three hour time point for calibrating the GlucoWatch® monitor, the mean percentage error (MPE) between the actual blood glucose and the calculated (MOE predicted) blood glucose was 13%.

In a diabetic study consisting of 61 patients, the diabetic subjects' blood glucose ranged from 23–389 mg/dl. A protocol was followed whereby a subject (who had fasted since the previous midnight) came to a test site where the GlucoWatch® monitor was applied to the subject, started, and calibrated. Over the next 14 hours, the subject had normal meals and a finger prick blood sample was taken every 20 minutes for glucose determination ("actual glucose"). Blood glucose levels were measured using the HemoCue® meter (HemoCue AB, Sweden), which has an accuracy of ±10%.

Figure 3:
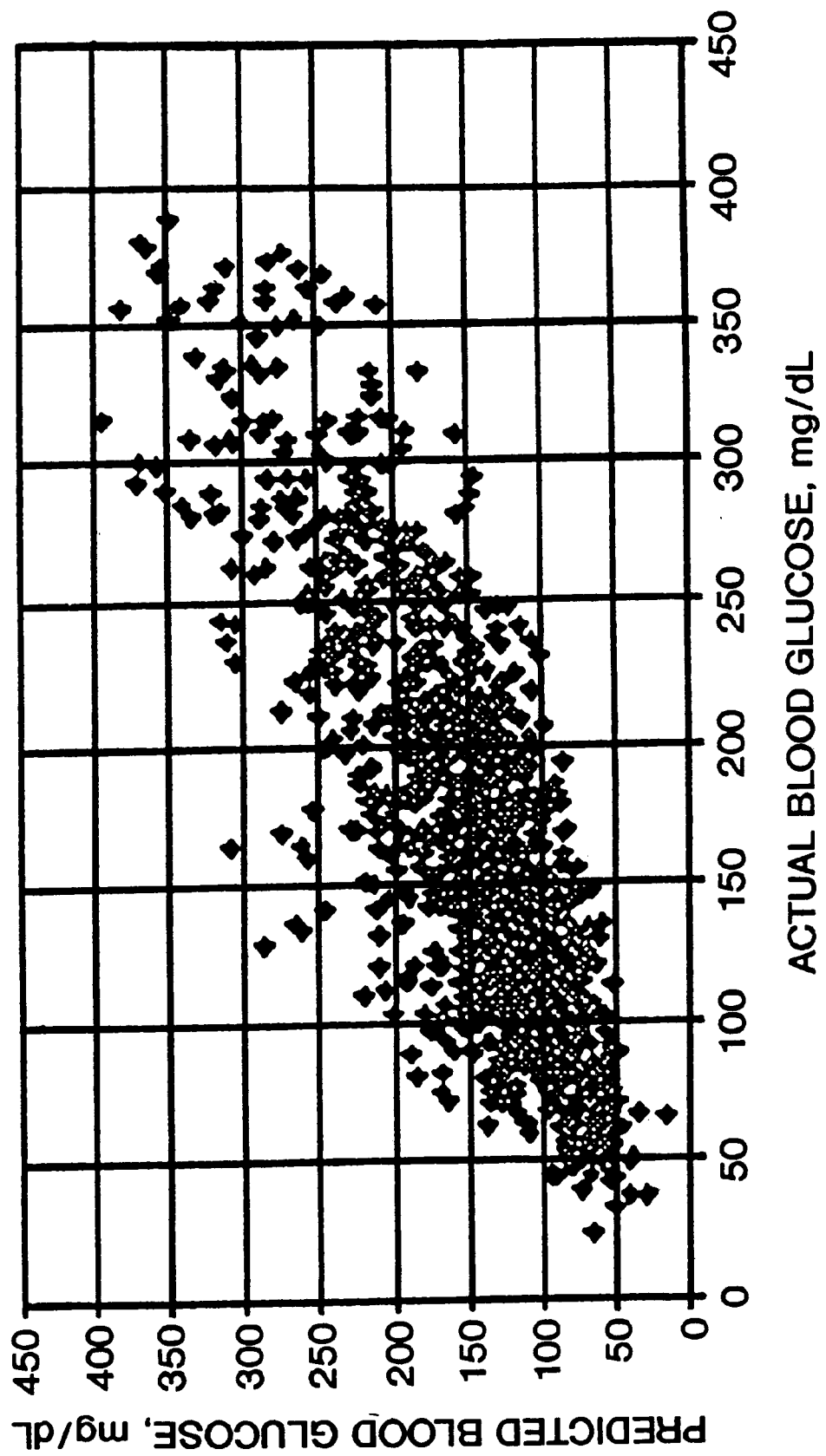
FIG. 3 depicts predicted blood glucose data (using the Mixtures of Experts algorithm) versus measured blood glucose data.

A plot of the glucose levels predicted by the Mixtures of Experts algorithm (based on the data described above) versus the actual blood glucose levels is presented in FIG. 3 (an Error Grid Plot). Analysis of the data shown in FIG. 3 showed a slope of 0.88, an intercept of 14, and a correlation coefficient of R=0.93. There were N=1,348 points comprising the Error Grid Plot.

These statistical results, along with the MPE=0.13 (discussed above), show the excellent predictive capabilities of the GlucoWatch® monitor and the Mixtures of Experts algorithm.

Although preferred embodiments of the subject invention have been described in some detail, it is understood that obvious variations can be made without departing from the spirit and the scope of the invention as defined by the appended claims.

What is claimed is:

1. A method for continually or continuously measuring an analyte present in a biological system, said method comprising:
   (a) transdermally extracting the analyte from the biological system using a sampling system that is in operative contact with a skin or mucosal surface of said biological system;
   (b) obtaining a raw signal from the extracted analyte, wherein said raw signal is specifically related to the analyte;
   (c) performing a calibration step which correlates the raw signal obtained in step (b) with a measurement value indicative of the concentration of analyte present in the biological system at the time of extraction;
   (d) repeating steps (a)–(b) to obtain a series of measurement values at selected time intervals, wherein the sampling system is maintained in operative contact with the skin or mucosal surface of said biological system to provide for a continual or continuous analyte measurement; and
   (e) predicting a measurement value based on the series of measurement values using the Mixtures of Experts algorithm, where the individual experts have a linear form $$An = \sum_{i=1}^{n} An_i w_i \quad (1)$$

wherein (An) is an analyte of interest, n is the number of experts, $An_i$ is the analyte predicted by Expert i; and $w_i$ is a weighting value, and the individual experts $An_i$ are further defined by the expression shown as Equation (2)

$$An_i = \sum_{j=1}^{m} a_{ij} P_j + z_i \quad (2)$$

wherein, $An_i$ is the analyte predicted by Expert i; $P_j$ is one of m parameters, m is typically less than 100; $a_{ij}$ are coefficients; and $z_i$ is a constant; and further where the weighting value, $w_i$, is defined by the formula shown as Equation (3)

$$w_i = \frac{e^{d_i}}{\left[\sum_{k=1}^{n} e^{d_k}\right]} \quad (3)$$

where e refers to than exponential function and the $d_k$ (note that the $d_i$ in the numerator of Equation 3 is one of the $d_k$) are a parameter set analogous to Equation 2 that is used to determine the weights $w_i$, The $d_k$ are given by Equation 4

$$d_k = \sum_{j=1}^{m} \alpha_{jk} P_j + \omega_k \quad (4)$$

where $\alpha_{jk}$ is a coefficient, $P_j$ is one of m parameters, and where $\omega_k$ is a constant.

2. The method of claim 1, wherein the analyte is extracted from the biological system in step (a) into a collection reservoir to obtain a concentration of the analyte in said reservoir.

3. The method of claim 2, wherein the collection reservoir is in contact with the skin or mucosal surface of the biological system and the analyte is extracted using an iontophoretic current applied to said skin or mucosal surface.

4. The method of claim 3, wherein the collection reservoir contains an enzyme that reacts with the extracted analyte to produce an electrochemically detectable signal.

5. The method of claim 4, wherein the analyte is glucose.

6. The method of claim 5, wherein the enzyme is glucose oxidase.

7. The method of claim 1, wherein the prediction of step (e) is carried out using said series of two or more measurement values in an algorithm represented by the Mixtures of Experts algorithm, where the individual experts have a linear form $$BG = w_1 BG_1 + w_2 BG_2 + w_3 BG \quad (5)$$

wherein (BG) is blood glucose, there are three experts (n=3) and $BG_i$ is the analyte predicted by Expert i; $w_i$ is a weighting value, and the individual Experts $BG_i$ are further defined by the expression shown as Equations 6, 7, and 8

$$BG_1 = p_1(\text{time}) + q_1(\text{active}) + r_1(\text{signal}) + s_1(BG|cp) + t_1 \quad (6)$$

$$BG_2 = p_2(\text{time}) + q_2(\text{active}) + r_2(\text{signal}) + s_2(BG|cp) + t_2 \quad (7)$$

$$BG_3 = p_3(\text{time}) + q_3(\text{active}) + r_3(\text{signal}) + s_3(BG|cp) + t_3 \quad (8)$$

wherein, $BG_i$ is the analyte predicted by Expert i; parameters include, time (elapsed time), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 9, 10, and 11

$$w_1 = \frac{e^{d_1}}{e^{d_1} + e^{d_2} + e^{d_3}} \quad (9)$$

$$w_2 = \frac{e^{d_2}}{e^{d_1} + e^{d_2} + e^{d_3}} \quad (10)$$

-continued $$w_3 = \frac{e^{d_3}}{e^{d_1} + e^{d_2} + e^{d_3}} \quad (11)$$

where e refers to the exponential function and $d_i$ is a parameter set (analogous to Equations 6, 7, and 8) that are used to determine the weights $w_i$, given by Equations 9, 10, and 11, and $$d_1 = \tau_1(\text{time}) + \beta_1(\text{active}) + \gamma_1(\text{signal}) + \delta_1(BG|cp) + \epsilon_1 \quad (12)$$

$$d_2 = \tau_2(\text{time}) + \beta_2(\text{active}) + \gamma_2(\text{signal}) + \delta_2(BG|cp) + \epsilon_2 \quad (13)$$

$$d_3 = \tau_3(\text{time}) + \beta_3(\text{active}) + \gamma_3(\text{signal}) + \delta_3(BG|cp) + \epsilon_3 \quad (14)$$

where $\tau_i$, $\beta_i$, $\gamma_i$ and $\delta_i$ are coefficients, and where $\epsilon_i$ is a constant.

8. The method of claim 7, which includes further parameters for measurement values selected from the group consisting of temperature, iontophoretic voltage, and skin conductivity.

9. A method for measuring blood glucose in a subject, said method comprising:

(a) obtaining a raw signal from a sensing apparatus, wherein said raw signal is specifically related to the glucose detected by the sensing apparatus;

(b) performing a calibration step which correlates the raw signal obtained in step (a) with a measurement value indicative of the subject's blood glucose concentration;

(c) repeating step (a) to obtain a series of measurement values at selected time intervals; and (d) predicting a measurement value using the Mixtures of Experts algorithm, where the individual experts have a linear form:

$$An = \sum_{i=1}^{n} An_i w_i \quad (1)$$

wherein (An) is blood glucose value, n is the number of experts, $An_j$ is the blood glucose value predicted by Expert i; and $w_i$ is a weighting value, and the individual experts $An_i$ are further defined by the expression shown as Equation (2)

$$An_i = \sum_{j=1}^{m} a_{ij} P_j + z_i \quad (2)$$

wherein, $An_i$ is the blood glucose value predicted by Expert i; $P_j$ is one of m parameters, m is typically less than 100; $a_{ij}$ are coefficients; and $z_i$ is a constant; and further where the weighting value, $w_i$, is defined by the formula shown as Equation (3)

$$w_i = \frac{e^{d_i}}{\left[\sum_{k=1}^{n} e^{d_k}\right]} \quad (3)$$

where e refers to the exponential function and the $d_k$ (note that the $d_i$ in the numerator of Equation 3 is one of the $d_k$) are a parameter set analogous to Equation 2 that is used to determine the weights $w_i$, The $d_k$ are given by Equation 4

$$d_k = \sum_{j=1}^{m} \alpha_{jk} P_j + \omega_k \quad (4)$$

where $\alpha_{jk}$ is a coefficient, $P_j$ is one of m parameters, and where $\omega_k$ is a constant.

10. The method of claim 9, where in said Mixtures of Experts algorithm, the individual experts have a linear form $$BG = w_1 BG_1 + w_2 BG_2 + w_3 BG_3 \quad (5)$$

wherein (BG) is blood glucose, there are three experts (n=3) and $BG_i$ is the analyte predicted by Expert i; $w_i$ is a weighting value, and the individual Experts $BG_i$ are further defined by the expression shown as Equations 6, 7, and 8

$$BG_1 = p_1(\text{time}) + q_1(\text{active}) + r_1(\text{signal}) + s_1(BG|cp) + t_1 \quad (6)$$

$$BG_2 = p_2(\text{time}) + q_2(\text{active}) + r_2(\text{signal}) + s_2(BG|cp) + t_2 \quad (7)$$

$$BG_3 = p_3(\text{time}) + q_3(\text{active}) + r_3(\text{signal}) + s_3(BG|cp) + t_3 \quad (8)$$

wherein, $BG_i$ is the analyte predicted by Expert i; parameters include, time (elapsed time), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 9, 10, and 11

$$w_1 = \frac{e^{d_1}}{e^{d_1} + e^{d_2} + e^{d_3}} \quad (9)$$

$$w_2 = \frac{e^{d_2}}{e^{d_1} + e^{d_2} + e^{d_3}} \quad (10)$$

$$w_3 = \frac{e^{d_3}}{e^{d_1} + e^{d_2} + e^{d_3}} \quad (11)$$

where e refers to the exponential function and $d_i$ is a parameter set (analogous to Equations 6, 7, and 8) that are used to determine the weights $w_i$, given by Equations 9, 10, and 11, and $$d_1 = \tau_1(\text{time}) + \beta_1(\text{active}) + \gamma_1(\text{signal}) + \delta_1(BG|cp) + \epsilon_1 \quad (12)$$

$$d_2 = \tau_2(\text{time}) + \beta_2(\text{active}) + \gamma_2(\text{signal}) + \delta_2(BG|cp) + \epsilon_2 \quad (13)$$

$$d_3 = \tau_3(\text{time}) + \beta_3(\text{active}) + \gamma_3(\text{signal}) + \delta_3(BG|cp) + \epsilon_3 \quad (14)$$

where $\tau_i$, $\beta_i$, $\gamma_i$ and $\delta_i$ are coefficients, and where $\epsilon_i$ is a constant.

11. The method of claim 10, wherein the sensing apparatus is a near-IR spectrometer.

12. The method of claim 10, wherein the sensing means comprises a biosensor having an electrochemical sensing element.

13. A monitoring system for continually or continuously measuring an analyte present in a biological system, said system comprising, in operative combination:
(a) sampling means for continually or continuously extracting the analyte from the biological system, wherein said sampling means is adapted for extracting the analyte across a skin or mucosal surface of said biological system;
(b) sensing means in operative contact with the analyte extracted by the sampling means, wherein said sensing means obtains a raw signal from the extracted analyte and said raw signal is specifically related to the analyte; and
(c) microprocessor means in operative communication with the sampling moans and the sensing means, wherein said microprocessor means (i) is used to control the sampling means and the sensing means to obtain a series of raw signals at selected time intervals during a continual or continuous measurement period, (ii) correlate the raw signals with measurement values indicative of the concentration of analyte present in the biological system, and (iii) predict a measurement value using the Mixtures of Experts algorithm, where the individual experts have a linear form $$An = \sum_{i=1}^{n} An_i w_i \quad (1)$$

wherein (An) is an analyte of interest, n is the number of experts, $An_i$ is the analyte predicted by Expert i; and $w_i$ is a weighting value, and the individual experts $An_i$ are further defined by the expression shown as Equation (2)

$$An_i = \sum_{j=1}^{m} a_{ij} P_j + z_i \quad (2)$$

wherein, $An_i$ is the analyte predicted by Expert i; $P_j$ is one of m parameters, m is typically less than 100; $a_{ij}$ are coefficients; and $z_i$ is a constant; and further where the weighting value, $w_i$, is defined by the formula shown as Equation (3)

$$w_i = \frac{e^{d_i}}{\left[\sum_{k=1}^{n} e^{d_k}\right]} \quad (3)$$

where e refers to the exponential function and the $d_k$ (note that the $d_i$ in the numerator of Equation 3 is one of the $d_k$) are a parameter set analogous to Equation 2 that is used to determine the weights $w_i$, The $d_k$ are given by Equation 4

$$d_k = \sum_{j=1}^{m} \alpha_{jk} P_j + \omega_k \quad (4)$$

where $\alpha_{jk}$ is a coefficient, $P_j$ is one of m parameters, and where $\omega_k$ is a constant.

14. The monitoring system of claim 13, wherein the sampling means includes one or more collection reservoirs for containing the extracted analyte.

15. The monitoring system of claim 14, wherein the sampling means uses an iontophoretic current to extract the analyte from the biological system.

16. The monitoring system of claim 15, wherein the collection reservoir contains an enzyme that reacts with the extracted analyte to produce an electrochemically detectable signal.

17. The monitoring system of claim 16, wherein the analyte is glucose and the enzyme is glucose oxidase.

18. A monitoring system for measuring blood glucose in a subject, said system comprising, in operative combination:
(a) sensing means in operative contact with the subject or with a glucose-containing sample extracted from the subject, wherein said sensing means obtains a raw signal specifically related to blood glucose in the subject; and
(b) microprocessor means in operative communication with the sensing means, wherein said microprocessor means (i) is used to control the sensing means to obtain a series of raw signals at selected time intervals, (ii) correlates the raw signals with measurement values indicative of the concentration of blood glucose present in the subject, and (iii) predicts a measurement value at a further time interval using the Mixtures of Experts algorithm, where the individual experts have a linear form $$BG = w_1 BG_1 + w_2 BG_2 + w_3 BG_3 \qquad (5)$$

wherein (BG) is blood glucose, there are three experts (n=3) and $BG_i$ is the analyte predicted by Expert i; $w_i$ is a weighting value, and the individual Experts $BG_i$ are further defined by the expression shown as Equations 6, 7, and 8

$$BG_1 = p_1(\text{time}) + q_1(\text{active}) + r_1(\text{signal}) + s_1(BG|cp) + t_1 \qquad (6)$$

$$BG_2 = p_2(\text{time}) + q_2(\text{active}) + r_2(\text{signal}) + s_2(BG|cp) + t_2 \qquad (7)$$

$$BG_3 = p_3(\text{time}) + q_3(\text{active}) + r_3(\text{signal}) + s_3(BG|cp) + t_3 \qquad (8)$$

wherein, $BG_i$ is the analyte predicted by Expert i; parameters include, time (elapsed time), active (active signal), signal (calibrated signal), and BG/cp (blood glucose value at a calibration point); $p_i$, $q_i$, $r_i$, and $s_i$ are coefficients; and $t_i$ is a constant; and further where the weighting value, $w_i$, is defined by the formulas shown as Equations 9, 10, and 11

$$w_1 = \frac{e^{d_1}}{e^{d_1} + e^{d_2} + e^{d_3}} \qquad (9)$$

$$w_2 = \frac{e^{d_2}}{e^{d_1} + e^{d_2} + e^{d_3}} \qquad (10)$$

$$w_3 = \frac{e^{d_3}}{e^{d_1} + e^{d_2} + e^{d_3}} \qquad (11)$$

where e refers to the exponential function and $d_i$ is a parameter set (analogous to Equations 6, 7, and 8) that are used to determine the weights $w_i$, given by Equations 9, 10, and 11, and $$d_1 = \tau_1(\text{time}) + \beta_1(\text{active}) + \gamma_1(\text{signal}) + \delta_1(BG|cp) + \epsilon_1 \qquad (12)$$

$$d_2 = \tau_2(\text{time}) + \beta_2(\text{active}) + \gamma_2(\text{signal}) + \delta_2(BG|cp) + \epsilon_2 \qquad (13)$$

$$d_3 = \tau_3(\text{time}) + \beta_3(\text{active}) + \gamma_3(\text{signal}) + \delta_3(BG|cp) + \epsilon_3 \qquad (14)$$

where $\tau_i$, $\beta_i$, $\gamma_i$ and $\delta_i$ are coefficients, and where $\epsilon_i$ is a constant.

19. The monitoring system of claim 18, which includes further parameters for raw signals selected from the group consisting of temperature, ionophoretic voltage, and skin conductivity.

20. The monitoring system of claim 18, wherein the sensing means comprises a biosensor having an electrochemical sensing element.

21. The monitoring system of claim 18, wherein the sensing means comprises a near-IR spectrometer.

* * * * *

UNITED STATES PATENT AND TRADEMARK OFFICE
CERTIFICATE OF CORRECTION

PATENT NO.   : 6,180,416 B1  
DATED        : January 30, 2001  
INVENTOR(S)  : Ronald T. Kurnik et al.

It is certified that error appears in the above-identified patent and that said Letters Patent is hereby corrected as shown below:

Column 19,
Line 42, "$BG=w_1BG_1+w_2BG_2+w_3BG$" should be -- $BG=w_1BG_1+w_2BG_2+w_3BG_3$ --;

Column 20,
Line 67, "the weights $w_i$, The" should be -- the weights $w_i$. The --;

Column 22,
Line 2, "sampling moans" should be -- sampling means --.

Signed and Sealed this

Twenty-fifth Day of December, 2001

Attest:

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO. : 6,180,416 B1
DATED : January 30, 2001
INVENTOR(S) : Ronald T. Kurnik et al.

It is certified that error appears in the above-identified patent and that said Letters Patent is hereby corrected as shown below:

Column 19,
Line 13, "the weights $w_i$. The" should read -- the weights $w_i$, the --.

Column 20,
Line 67, "the weights $w_i$. The" should read -- the weights $w_i$, the --.

Column 22,
Line 39, "the weights $w_i$. The" should read -- the weights $w_i$, the --.

Signed and Sealed this

Twenty-sixth Day of October, 2004

JON W. DUDAS
*Director of the United States Patent and Trademark Office*